United States Patent
Qiu et al.

(10) Patent No.: US 11,937,980 B2
(45) Date of Patent: Mar. 26, 2024

(54) MULTI-ROW ULTRASONIC IMAGING APPARATUS AND ULTRASONIC IMAGING INSTRUMENT

(71) Applicant: SHENZHEN INSTITUTES OF ADVANCED TECHNOLOGY, Shenzhen (CN)

(72) Inventors: Weibao Qiu, Shenzhen (CN); Min Su, Shenzhen (CN); Zhiqiang Zhang, Shenzhen (CN); Hairong Zheng, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 248 days.

(21) Appl. No.: 17/476,431

(22) Filed: Sep. 15, 2021

(65) Prior Publication Data
US 2022/0000450 A1   Jan. 6, 2022

Related U.S. Application Data

(63) Continuation of application No. PCT/CN2019/112998, filed on Oct. 24, 2019.

(30) Foreign Application Priority Data

Mar. 18, 2019  (CN) .......................... 201910204641.1

(51) Int. Cl.
*A61B 8/00* (2006.01)
(52) U.S. Cl.
CPC .......... *A61B 8/4461* (2013.01); *A61B 8/4477* (2013.01)

(58) Field of Classification Search
CPC ... A61B 8/4461; A61B 8/4477; A61B 8/4494; A61B 8/54; A61B 8/085
See application file for complete search history.

(56) References Cited

U.S. PATENT DOCUMENTS

| | | | | |
|---|---|---|---|---|
| 4,035,839 A | * | 7/1977 | Eggleton | A61B 8/15 73/618 |
| 4,633,882 A | * | 1/1987 | Matsuo | A61B 8/4461 600/146 |

(Continued)

FOREIGN PATENT DOCUMENTS

| | | |
|---|---|---|
| CN | 1901837 A | 1/2007 |
| CN | 102793980 A | 11/2012 |

(Continued)

OTHER PUBLICATIONS

International Search Report issued in corresponding International application No. PCT/CN2019/112998, dated Jan. 23, 2020.

(Continued)

*Primary Examiner* — Serkan Akar
*Assistant Examiner* — Gabriel Victor Popescu

(57) ABSTRACT

A multi-row ultrasonic imaging apparatus and an ultrasonic imaging instrument are disclosed. The multi-row ultrasonic imaging apparatus includes a housing, and a first ultrasonic transducer, a second ultrasonic transducer, and an adjustment mechanism that are installed in the housing. Ultrasonic waves emitted by the first ultrasonic transducer and the second ultrasonic transducer can intersect to form a confocal point. At least one of the first ultrasonic transducer and the second ultrasonic transducer is connected to the adjustment mechanism to move relative to the housing under the action of the adjustment mechanism, so as to adjust the position of the confocal point.

7 Claims, 4 Drawing Sheets

(56) References Cited

U.S. PATENT DOCUMENTS

| | | | |
|---|---|---|---|
| 5,501,655 | A | 3/1996 | Rolt et al. |
| 10,004,888 | B2 | 6/2018 | Chapelon et al. |
| 2015/0141734 | A1* | 5/2015 | Chapelon ................. A61D 1/00 600/2 |
| 2017/0360415 | A1* | 12/2017 | Rothberg ............. A61B 8/4477 |
| 2019/0099154 | A1* | 4/2019 | Adachi ................ A61B 8/4461 |

FOREIGN PATENT DOCUMENTS

| | | |
|---|---|---|
| CN | 103140261 A | 6/2013 |
| CN | 203519148 U | 4/2014 |
| CN | 104661600 A | 5/2015 |
| CN | 106730424 A | 5/2017 |
| CN | 106880908 A | 6/2017 |
| CN | 106964083 A | 7/2017 |
| CN | 107913477 A | 4/2018 |
| CN | 109770945 A | 5/2019 |
| EP | 2636428 A1 | 9/2013 |
| WO | 2006068689 A2 | 6/2006 |
| WO | 2015167894 A1 | 11/2015 |

OTHER PUBLICATIONS

Written Opinion of the International Search Authority in corresponding International application No. PCT/CN2019/112998.
First Office Action from China Patent Office in a counterpart Chinese Patent Application 201910204641.1, dated Feb. 7, 2020.
Second Office Action from China Patent Office in a counterpart Chinese Patent Application 201910204641.1, dated Jun. 28, 2020.

* cited by examiner

MULTI-ROW ULTRASONIC IMAGING APPARATUS AND ULTRASONIC IMAGING INSTRUMENT

CROSS-REFERENCE TO RELATED APPLICATIONS

This application is a U.S. continuation of co-pending International Patent Application Number PCT/CN2019/112998, filed on Oct. 24, 2019, which claims the benefit and priority of Chinese Patent Application Number 201910204641.1, filed on Mar. 18, 2019, with China National Intellectual Property Administration, the disclosures of which are incorporated herein by reference in their entireties.

TECHNICAL FIELD

This application relates to the technical field of medical equipment, and more particularly relates to a multi-row ultrasonic imaging apparatus and an ultrasonic imaging instrument.

BACKGROUND

Nowadays, in the treatment process of tumor ablation and ultrasonic drug delivery, it is needed to precisely control the confocal point of ultrasound to prevent the destruction of healthy tissue cells which may otherwise cause internal bleeding or other negative symptoms. However, most of the current ultrasonic devices are dual-frequency confocal transducers with a fixed confocal point. They can only change the confocal point by manually moving the position of the transducer, hence complicated operation and low precision. Furthermore, when a high-frequency transducer is stacked in front of a low-frequency transducer, due to the occlusion of the high-frequency transducer, the propagation of the sound waves emitted by the low-frequency transducer will be affected, thus reducing the performance of the low-frequency transducer.

In view of this, it is particularly important to design and manufacture a multi-row ultrasonic imaging apparatus and ultrasonic imaging instrument capable of precise zooming, especially in the production of medical devices.

SUMMARY

It is therefore an objective of the present application to provide a multi-row ultrasonic imaging apparatus that can accurately change the position of the confocal point, and the multiple rows of transducers will not affect each other, which is practical and efficient.

Another object of the present application is to provide an ultrasound imaging instrument that can accurately change the position of the confocal point, and where multiple rows of transducers will not affect each other, which is practical, efficient, and cost-effective.

In order to solve the above problems, this application provides the following technical solutions.

A multi-row ultrasonic imaging apparatus includes a housing, and a first ultrasonic transducer, a second ultrasonic transducer, and an adjustment mechanism that are installed in the housing. The ultrasonic waves emitted by the first ultrasonic transducer and the second ultrasonic transducer can intersect to form a confocal point. At least one of the first ultrasonic transducer and the second ultrasonic transducer is connected to the adjustment mechanism to move relative to the housing under the action of the adjustment mechanism, thereby adjusting the position of the confocal point.

In a further technical solution adopted in the embodiments according to the present application, the adjustment mechanism includes a displacement mechanism. The first ultrasonic transducer is fixedly installed in the housing, and the second ultrasonic transducer is connected with the housing through the displacement mechanism.

In a further technical solution adopted in the embodiments according to the present application, the displacement mechanism includes a screw rod and a nut. The screw rod extends into the housing and is rotatably connected with the housing and fitted with the nut. The second ultrasonic transducer is movably connected with the nut. The nut is operative to drive the second ultrasonic transducer to approach the first ultrasonic transducer or away from the first ultrasonic transducer.

In a further technical solution adopted in the embodiments according to the present application, the displacement mechanism further includes a drive member, which is fixedly installed on the housing and connected with the screw rod.

In a further technical solution adopted in the embodiments according to the present application, the adjustment mechanism includes a limiting shaft and a rotary mechanism, and the second ultrasonic transducer is connected to the limiting shaft through the rotary mechanism.

In a further technical solution adopted in the embodiments according to the present application, the rotary mechanism includes a rotary motor and a transmission member. The transmission member includes a first gear and a second gear. The rotary motor is fixedly mounted on the second ultrasonic transducer. The first gear is sleeved on an output shaft of the rotary motor and is fixedly connected to the output shaft. The second ultrasonic transducer is sleeved on the limiting shaft and is rotatable relative to the limiting shaft. The second gear is sleeved on the limiting shaft and is fixedly connected to the limiting shaft. The first gear meshes with the second gear.

In a further technical solution adopted in the embodiments according to the present application, a limiting slot is further defined in the housing, and the limiting shaft extends into the limiting slot and is in a sliding fit with the limiting slot.

In a further technical solution adopted in the embodiments according to the present application, the multi-row ultrasonic imaging apparatus further includes a third ultrasonic transducer. The first ultrasonic transducer is arranged in the middle of the housing. The third ultrasonic transducer is arranged on a side of the first ultrasonic transducer far away from the second ultrasonic transducer, and is connected with the adjustment mechanism.

In a further technical solution adopted in the embodiments according to the present application, the first ultrasonic transducer and the second ultrasonic transducer are both array ultrasonic transducers, and the number of array elements of each of the first ultrasonic transducer and the second ultrasonic transducer lie in the range of 96-256.

An ultrasonic imaging instrument is further provided that includes a control system and the above-mentioned multi-row ultrasonic imaging apparatus. The multi-row ultrasonic imaging apparatus includes a housing, and a first ultrasonic transducer, a second ultrasonic transducer, and an adjustment mechanism that are installed in the housing. The ultrasonic waves emitted by the first ultrasonic transducer and the second ultrasonic transducer can intersect to form a confocal point. At least one of the first ultrasonic transducer and the second ultrasonic transducer is connected to the adjustment mechanism to move relative to the housing under the action of the adjustment mechanism, thereby adjusting the position of the confocal point. The control system is coupled to each of the first ultrasonic transducer and the second ultrasonic transducer.

The multi-row ultrasonic imaging apparatus and ultrasonic imaging instrument provided by the present application provide the following benefits.

In the multi-row ultrasonic imaging apparatus provided by the present application, the ultrasonic waves emitted by the first ultrasonic transducer and the second ultrasonic transducer can intersect to form a confocal point. At least one of the first ultrasonic transducer and the second ultrasonic transducer is connected to the adjustment mechanism to move relative to the housing under the action of the adjustment mechanism, thereby adjusting the position of the confocal point. Compared with the related art, the multi-row ultrasonic imaging apparatus provided by the present application adopts an adjustment mechanism connected with the first ultrasonic transducer and/or the second ultrasonic transducer, so it can accurately change the position of the confocal point. In addition, the multiple rows of transducers will not affect each other, which is practical and efficient.

The ultrasound imaging instrument provided by the present application includes the multi-row ultrasound imaging apparatus, and can precisely change the position of the confocal point, and the multi-row transducers will not affect each other, which is practical, efficient, and cost-effective.

BRIEF DESCRIPTION OF DRAWINGS

For a better understanding of the technical solutions of the embodiments according to the present application, hereinafter the drawings that need to be used in the embodiments disclosed herein will be briefly described. It will be appreciated that the following drawings merely show some embodiments of the present application, and therefore should not be regarded as limiting the scope. For those having ordinary skill in the art, other related drawings may also be obtained based on these drawings without investing creative efforts.

Figure 1:
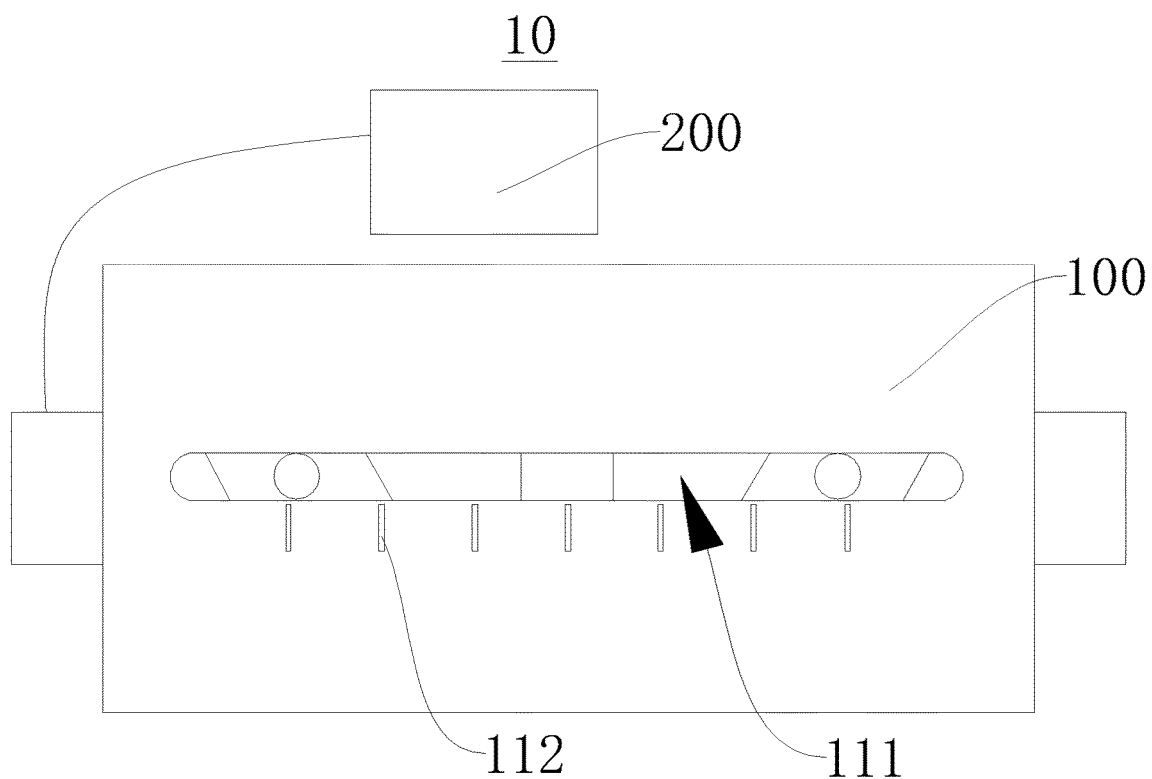
FIG. 1 is a schematic diagram of an ultrasonic imaging instrument provided by an embodiment of the application.

Reference signs shown in the drawings: 10—Ultrasonic imaging instrument; 100—Multi-row ultrasonic imaging apparatus; 110—Housing; 111—Limiting slot; 112—Scale line; 113—First sidewall; 114—Second sidewall; 115—Third sidewall; 116—Fourth sidewall; 117—Bottom wall; 120—First ultrasonic transducer; 121—Groove; 122—Limiting stand; 130—Second ultrasonic transducer; 140—Third ultrasonic transducer; 150—First displacement mechanism; 151—Drive member; 152—Movable member; 154—Screw rod; 155—Nut; 160—First rotary mechanism; 161—Rotary motor; 162—Transmission member; 163—First gear; 164—Second gear; 165—Output shaft; 170—Second displacement mechanism; 180—Second rotary mechanism; 190—Limiting shaft; 200—Control system.

DETAILED DESCRIPTION OF ILLUSTRATIVE EMBODIMENTS

For a better understanding of the purposes, technical solutions and advantages of the embodiments according to the present application, hereinafter technical solutions in the embodiments according to the present application will be described in a definite and comprehensive manner in connection with the accompanying drawings in the embodiments according to the application. Apparently, the embodiments described herein are only a part, rather than all of the embodiments in accordance with the present application. The components or parts of the embodiments of the present application generally described and shown in the drawings herein may be arranged and designed in various different configurations.

Therefore, the following detailed description of the embodiments of the application provided in the accompanying drawings is not intended to limit the scope of protection of the application, but merely represents some illustrative embodiments of the application. Based on the embodiments of the present application, all other embodiments obtained by those having ordinary skill in the art without investing creative efforts shall all fall in the scope of protection of the present application.

It should be noted that similar reference numerals and characters indicate similar items in the following drawings. Thus, once an item is defined in one drawing, it does not need to be further defined and explained in the subsequent drawings.

As used herein, terms "inner", "in", "inside", "outer", "outside", "upper", "lower", "horizontal", or the like are used to indicate orientational or relative positional relationships based on those illustrated in the drawings, or the orientational or positional relationship that the product of the invention is usually placed in use. They are merely intended for simplifying the description of the present disclosure, rather than indicating or implying that the device or element referred to must have a particular orientation or be constructed and operate in a particular orientation. Therefore, these terms are not to be construed as restricting the present disclosure. In addition, terms "first", "second", "third", or the like are merely used for purposes of distinguishing, and are to be understood as indicating or implying relative importance.

Furthermore, as used herein, terms "disposed on", "arranged on", "connected to", "coupled to", "mounted on", "installed on", "connected with", and "coupled with" should be understood in a broad sense unless otherwise specified and defined. For example, they may indicate a fixed connection, a detachable connection, or an integral connection. They may denote a mechanical connection, or an electrical connection. They may denote a direct connection, a connection through an intermediate, or an internal connection between two elements. For those of ordinary skill in the art, the specific meanings of the above terms as used in the present application can be understood depending on specific contexts.

Hereinafter, some embodiments of the present application will be described in detail with reference to the accompanying drawings. In the case of no conflict or contradiction, the features described in the following embodiments may be combined with each other.

Embodiment

Referring to FIG. 1, an embodiment of the present application provides an ultrasonic imaging instrument 10 for obtaining an image of an organ in a patient's body. The ultrasonic imaging instrument 10 can precisely change the position of the confocal point. It can obtain multi-angle imaging at the same time. It can also use one transducer for excitation and another transducer for reception to achieve harmonic or radiation force imaging. Furthermore, the multiple rows of transducers will not affect each other, which is practical, efficient, and cost-effective. In addition, because multiple rows of transducers are used, and the frequency of each transducer can be different, it is also made possible that ultrasonic waves of different frequencies act on one focal point at the same time to achieve the purpose of multifrequency ultrasonic focusing.

The ultrasound imaging instrument 10 includes a control system 200 and a multi-row ultrasound imaging apparatus 100. The multi-row ultrasonic imaging apparatus 100 can emit multiple rows of ultrasonic waves and form a confocal point, and can also adjust the position of the confocal point. The control system 200 is coupled to the multi-row ultrasonic imaging apparatus 100, and can obtain multiple imaging sections by using the multiple rows of transducers in the multi-row ultrasonic imaging apparatus 100. Alternatively or additionally, the control system 200 may use part of the transducers in the multi-row ultrasonic imaging apparatus 100 to send ultrasonic waves, and then use the remaining transducers to receive the ultrasonic waves, so as to perform frequency conversion imaging.

Figure 2:
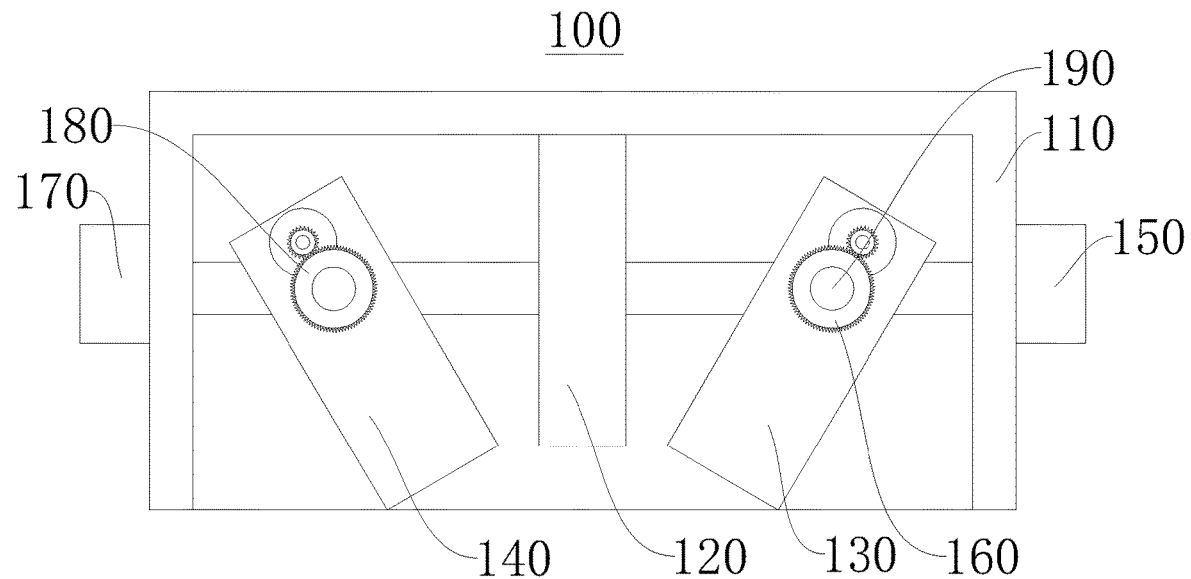
FIG. 2 is a schematic diagram of a multi-row ultrasonic imaging apparatus provided by an embodiment of the application.
Figure 3:
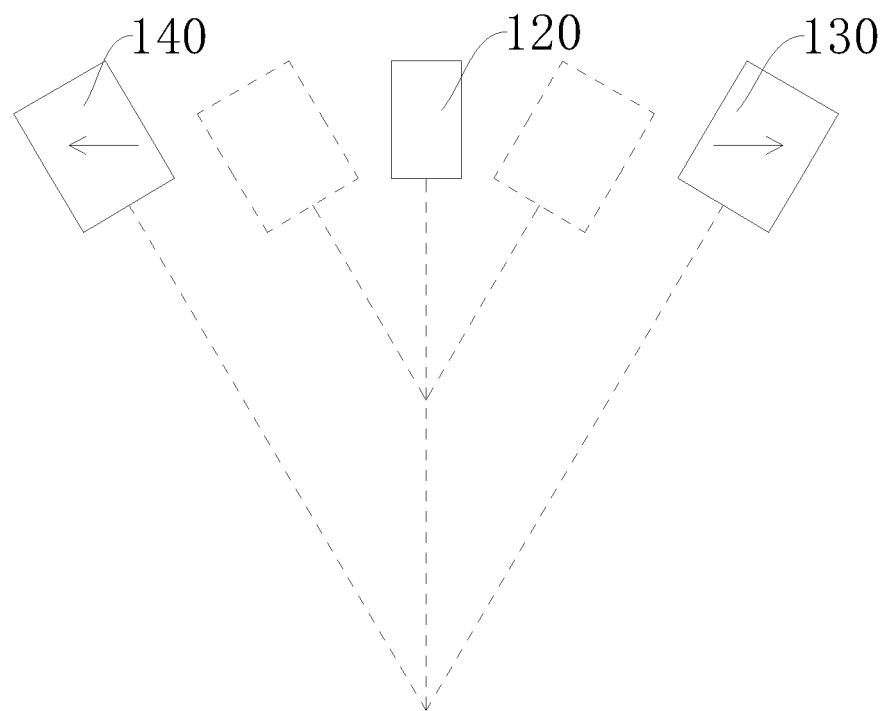
FIG. 3 is a schematic diagram illustrating that the ultrasonic waves emitted by the multiple rows of transducers in the multi-row ultrasonic imaging apparatus provided by an embodiment of the application converge at one point after translation.
Figure 4:
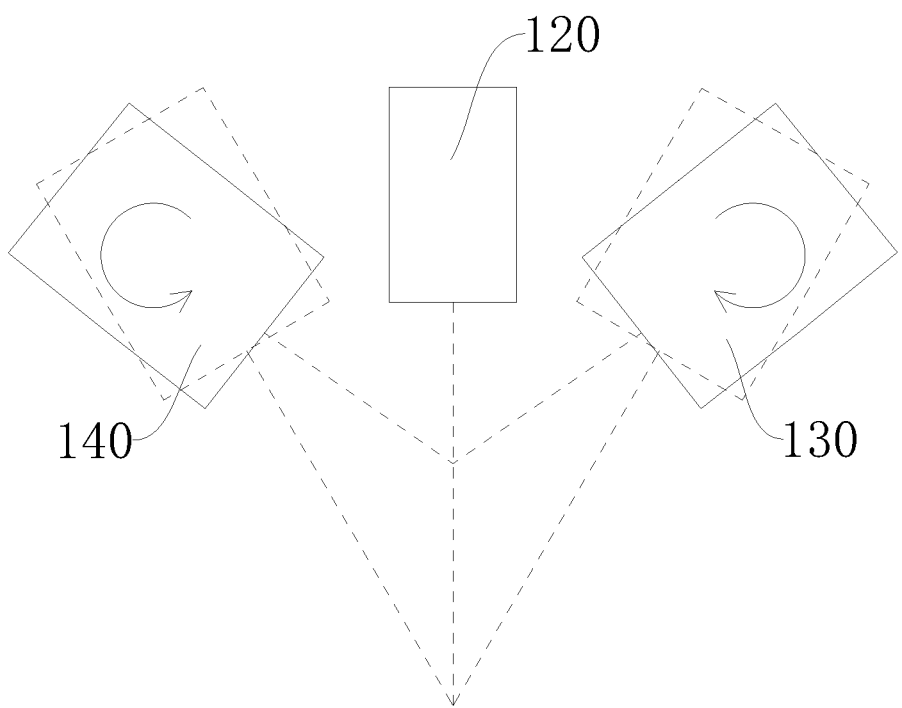
FIG. 4 is a schematic diagram illustrating that the ultrasonic waves emitted by the multiple rows of transducers in the multi-row ultrasonic imaging apparatus provided by an embodiment of the application converge at one point after rotation.

Referring to FIGS. 2, 3 and 4 in conjunction, where the dotted lines shown in FIG. 3 indicate the positions of the second ultrasonic transducer 130 and the third ultrasonic transducer 140 before translation and the direction of extension of the ultrasonic waves emitted by the multiple rows of transducers, and the dotted lines shown in FIG. 4 indicate the positions of the second ultrasonic transducer 130 and the third ultrasonic transducer 140 before rotation and the direction of extension of the ultrasonic waves emitted by the multiple rows of transducers. The multi-row ultrasonic imaging apparatus 100 includes a housing 110, a first ultrasonic transducer 120, a second ultrasonic transducer 130, a third ultrasonic transducer 140, and two adjustment mechanisms (not shown). The transducers come in the number of three. Among them, the first ultrasonic transducer 120 is fixedly installed in the housing 110 and arranged in the middle of the housing 110. The second ultrasonic transducer 130 is arranged on one side of the first ultrasonic transducer 120 and is connected to an adjusting mechanism so as to be able to move relative to the housing 110 under the action of the adjustment mechanism. The third ultrasonic transducer 140 is arranged on a side of the first ultrasonic transducer 120 away from the second ultrasonic transducer 130 and is connected to another adjustment mechanism so as to be able to move relative to the housing 110 under the action of the adjustment mechanism. The ultrasonic waves emitted by the first ultrasonic transducer 120, the second ultrasonic transducer 130, and the third ultrasonic transducer 140 can intersect at a point, which is the confocal point.

In particular, the movement of the second ultrasonic transducer 130 relative to the housing 110 means that the second ultrasonic transducer 130 translates and/or rotates relative to the housing 110; that is, the second ultrasonic transducer 130 can translate relative to the housing 110, rotate relative to the housing 110, and can also both translate and rotate relative to the housing 110. In the same way, the movement of the third ultrasonic transducer 140 relative to the housing 110 refers to the translation and/or rotation of the third ultrasonic transducer 140 relative to the housing 110.

It should be noted that the control system 200 is connected to each of the first ultrasonic transducer 120, the second ultrasonic transducer 130, and the third ultrasonic transducer 140, so as to obtain three imaging sections by using the first ultrasonic transducer 120, the second ultrasonic transducer 130, and the third ultrasonic transducer 140. However, the present application will not be limited to thereto. In other embodiments, the control system 200 may also use the first ultrasonic transducer 120 to send ultrasonic waves, and then use the second ultrasonic transducer 130 and the third ultrasonic transducer 140 to receive ultrasonic waves, so as to perform frequency conversion imaging.

In this embodiment, the control system 200 is separately connected with two adjustment mechanisms in order to electrically control the position of the second ultrasonic transducer 130 and the third ultrasonic transducer 140 to change, thereby controlling the position of the confocal point formed by the first ultrasonic transducer 120, the second ultrasonic transducer 130, and the third ultrasonic transducer 140 to change. However, the present application will not be limited to this. In other embodiments, the second ultrasonic transducer 130 and the third ultrasonic transducer 140 may also be manually translated or rotated to adjust the positions of the second ultrasonic transducer 130 and the third ultrasonic transducer 140, thereby adjusting the position of the confocal point. For example, a slide rail may be arranged in the housing 110, and the second ultrasonic transducer 130 and the third ultrasonic transducer 140 are slidably arranged on the slide rail, so that the user can manually push the second ultrasonic transducer 130 and the third ultrasonic transducer 140 to be translated. For another example, two rotary columns capable of rotating relative to the housing 110 may be arranged in the housing 110, the second ultrasonic transducer 130 is installed on one rotary column, and the third ultrasonic transducer 140 is installed on the other rotary column, so that the user can manually twist the rotary column to rotate the second ultrasonic transducer 130 and the third ultrasonic transducer 140.

It should be noted that the adjustment mechanism includes a limiting shaft 190, a displacement mechanism and a rotary mechanism. Then two adjustment mechanisms would include two limiting shafts 190, two displacement mechanisms and two rotary mechanisms. In order to facilitate the description below, the displacement mechanism and the rotation mechanism connected to the second ultrasonic transducer 130 are respectively named the first displacement mechanism 150 and the first rotary mechanism 160, the displacement mechanism and the rotary mechanism connected to the third ultrasonic transducer 140 are respectively named the second displacement mechanism 170 and the second rotary mechanism 180. Both the first displacement mechanism 150 and the first rotary mechanism 160 are connected to the second ultrasonic transducer 130 through a limiting shaft 190. Both the second displacement mechanism 170 and the second rotary mechanism 180 are connected to the third ultrasonic transducer 140 through another limiting shaft 190. In this embodiment, the movements of the first displacement mechanism 150 and the second displacement mechanism 170 are kept in reverse synchronization, and the movements of the first rotary mechanism 160 and the second rotary mechanism 180 are also kept in reverse synchronization, so that the distance between the first ultrasonic transducer 120 and the second ultrasonic transducer 130 and the distance between the first ultrasonic transducer 120 and the third ultrasonic transducer 140 are always kept equal, and that the angle formed by the first ultrasonic transducer 120 and the second ultrasonic transducer 130 is always kept the same as the angle formed by the first ultrasonic transducer 120 and the third ultrasonic transducer 140. As a result, the ultrasonic waves emitted by the first ultrasonic transducer 120, the second ultrasonic transducer 130, and the third ultrasonic transducer 140 always converge at a common focal point.

It should be noted that in other embodiments, the third ultrasonic transducer 140, the second displacement mechanism 170, and the second rotary mechanism 180 may not be included. In this case, the first displacement mechanism 150 and the first rotary mechanism 160 can drive the second ultrasonic transducer 130 to move, so that the position of the confocal point formed by the first ultrasonic transducer 120 and the second ultrasonic transducer 130 can be changed.

Figure 5:
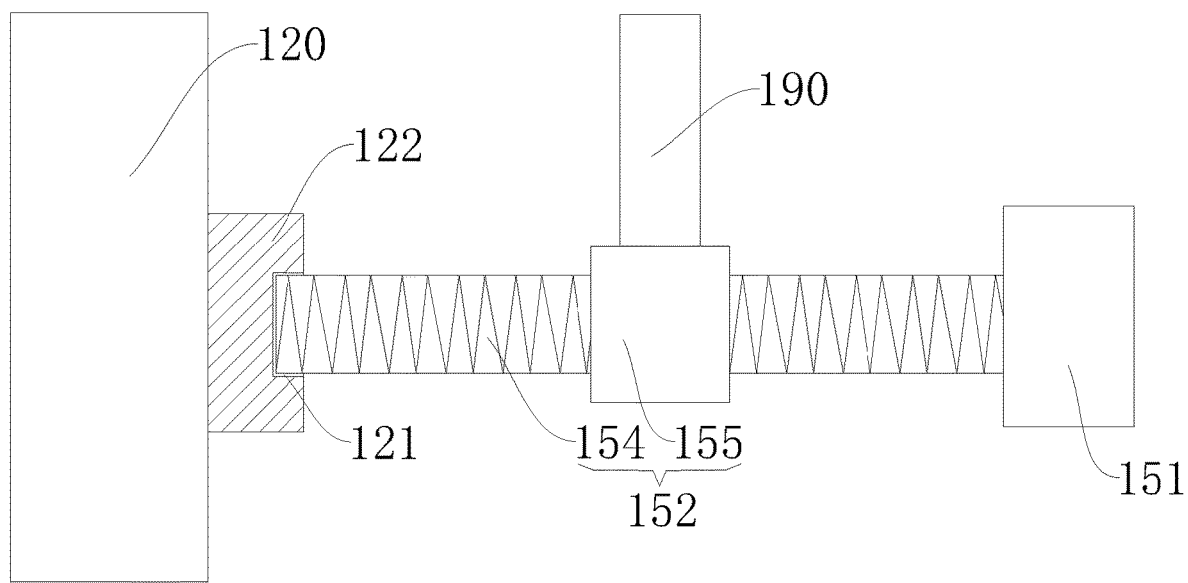
FIG. 5 is a schematic diagram of a first displacement mechanism in a multi-row ultrasonic imaging apparatus provided by an embodiment of the application.

As illustrated in FIG. 5, the first displacement mechanism 150 includes a drive member 151 and a movable member 152. The drive member 151 is fixedly installed on the housing 110 and connected to the movable member 152 to drive the movable member 152 to translate. The movable member 152 extends into the housing 110 and is fixedly connected to the limiting shaft 190. The movable member 152 can be driven by the drive member 151 to approach or move away from the first ultrasonic transducer 120. The second ultrasonic transducer 130 is sleeved outside the limiting shaft 190 and can rotate relative to the limiting shaft 190. The movable member 152 can drive the second ultrasonic transducer 130 to approach or move away from the first ultrasonic transducer through the limiting shaft 190. During this process, the second ultrasonic transducer 130 is translated along the direction of extension of the movable member 152, so that the confocal position formed by the first ultrasonic transducer 120 and the second ultrasonic transducer 130 is changed. The control system 200 is coupled to the drive member 151 to control the drive member 151 to start or pause.

In this embodiment, the drive member 151 may be a motor. The movable member 152 may include a screw rod 154 and a nut 155. The drive member 151 is connected to the screw rod 154 to drive the screw rod 154 to rotate. The screw rod 154 extends into the housing 110, is rotatably connected with the housing 110, and is fitted with the nut 155. The nut 155 can translate along the axial direction of the screw rod 154 during the rotation of the screw rod 154. The limiting shaft 190 is fixedly connected to an outer side of the nut 155, which can drive the limiting shaft 190 to move, thereby driving the second ultrasonic transducer 130 to translate along the axial direction of the screw rod 154. However, the present application will not be limited to thereto. In other embodiments, the drive member 151 may be an electric push rod, a hydraulic cylinder, or a hydraulic motor, etc., and the movable member 152 may be a gear and a rack, which can also drive the limiting shaft 190 to move in the housing 110, so that the second ultrasonic transducer 130 is translated and the position of the confocal point is changed.

It should be noted that the side surface of the first ultrasonic transducer 120 is fixedly connected to a limiting stand 122, which defines a groove 121, and the screw rod 154 extends into the groove 121 and can rotate relative to the groove 121. When the position of the second ultrasonic transducer 130 needs to be adjusted, the drive member 151 drives the screw rod 154 to rotate. One end of the screw rod 154 rotates relative to the housing 110, and the other end rotates relative to the groove 121. The groove 121 can limit the screw rod 154 to prevent the screw rod 154 from falling off. In this process, the nut 155 rotates relative to the screw rod 154 to translate in the axial direction of the screw rod 154, and drives the second ultrasonic transducer 130 to approach or move away from the first ultrasonic transducer 120 through the limiting shaft 190.

The specific structure of the second displacement mechanism 170 is the same as that of the first displacement mechanism 150, and thus is not to be detailed herein again. The second displacement mechanism 170 can drive the third ultrasonic transducer 140 to approach or move away from the first ultrasonic transducer 120.

Figure 6:
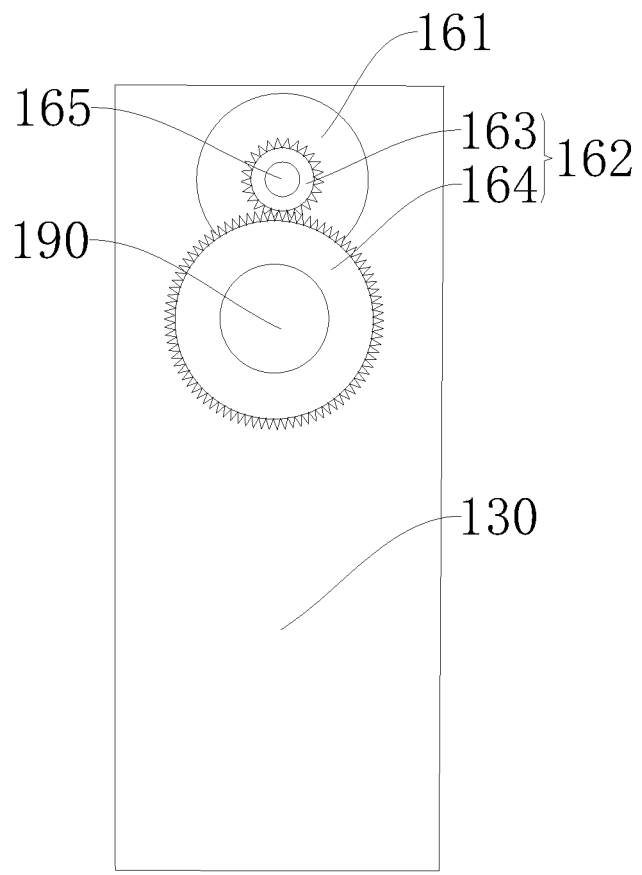
FIG. 6 is a schematic diagram of a first rotary mechanism in a multi-row ultrasonic imaging apparatus provided by an embodiment of the application.

Referring to FIG. 6, the first rotary mechanism 160 includes a rotary motor 161 and a transmission member 162. The rotary motor 161 is fixedly mounted on the second ultrasonic transducer 130 and is connected to the limiting shaft 190 through the transmission member 162. The rotary motor 161 can drive the second ultrasonic transducer 130 to rotate relative to the limiting shaft 190 through the transmission member 162 so that the angle between the first ultrasonic transducer 120 and the second ultrasonic transducer 130 becomes larger or smaller, thereby changing the position of the confocal point formed by the first ultrasonic transducer 120 and the second ultrasonic transducer 130. The control system 200 is coupled to the rotary motor 161 to control the rotational speed and the rotational direction of the rotary motor 161. In this embodiment, the range of rotation of the second ultrasonic transducer 130 lies in the range between 0 and 90 degrees.

In this embodiment, the transmission member 162 includes a first gear 163 and a second gear 164. The first gear 163 is sleeved outside the output shaft 165 of the rotary motor 161 and is fixedly connected to the output shaft 165. The second gear 164 is sleeved outside the limiting shaft 190 and fixedly connected to the limiting shaft 190, where the first gear 163 meshes with the second gear 164. The rotary motor 161 may be started, causing the output shaft 165 to rotate, which in turn drives the first gear 163 to rotate. At this time, because the limiting shaft 190 is fixedly connected to the nut 155, the limiting shaft 190 does not rotate, and so the second gear 164 also does not rotate, and further because the first gear 163 meshes with the second gear 164, the rotary motor 161 will rotate under the reaction force, thereby driving the second ultrasonic transducer 130 to rotate.

The specific structure of the second rotary mechanism 180 is the same as that of the first rotary mechanism 160, and thus is not to be detailed herein again. The second rotary mechanism 180 can drive the third ultrasonic transducer 140 to rotate relative to the first rotary mechanism 160.

In this embodiment, the first ultrasonic transducer 120, the second ultrasonic transducer 130, and the third ultrasonic transducer 140 are all array ultrasonic transducers, and the number of array elements of each of the first ultrasonic transducer 120, the second ultrasonic transducer 130, and the third ultrasonic transducer 140 lies in the range between 96 and 256. The first ultrasonic transducer 120 has a higher frequency than that of the second ultrasonic transducer 130, which in turn has the same frequency as that of the third ultrasonic transducer 140. However, the present application will not be limited thereto. In other embodiments, the frequencies of the multiple rows of transducers may also be different, or they may all be the same, so as to adapt to different scenarios.

Continue to refer to FIG. 1, it is worth noting that the housing 110 may define a limiting slot 111, the direction of extension of which is the same as that of the movable member 152. The limiting shaft 190 passes through the second ultrasonic transducer 130, extends into the limiting slot 111 and is slidably fitted with the limiting slot 111. The limiting slot 111 can limit the limiting shaft 190 to prevent the nut 155 from rotating along with the screw rod 154. In addition, the limiting slot 111 can limit the extreme position of the limiting shaft 190 to prevent the limiting shaft 190 from detaching from the housing 110.

In this embodiment, the limiting slot 111 is a through slot, and the limiting shaft 190 can pass through the limiting slot 111 to facilitate the user to observe the position of the limiting shaft 190. Scale lines 112 are provided on the housing 110, and are arranged on one side of the limiting slot 111, so that the user can know the specific position of the limiting shaft 190 through the scale lines 112, thus observing the depth of the confocal point.

Figure 7:
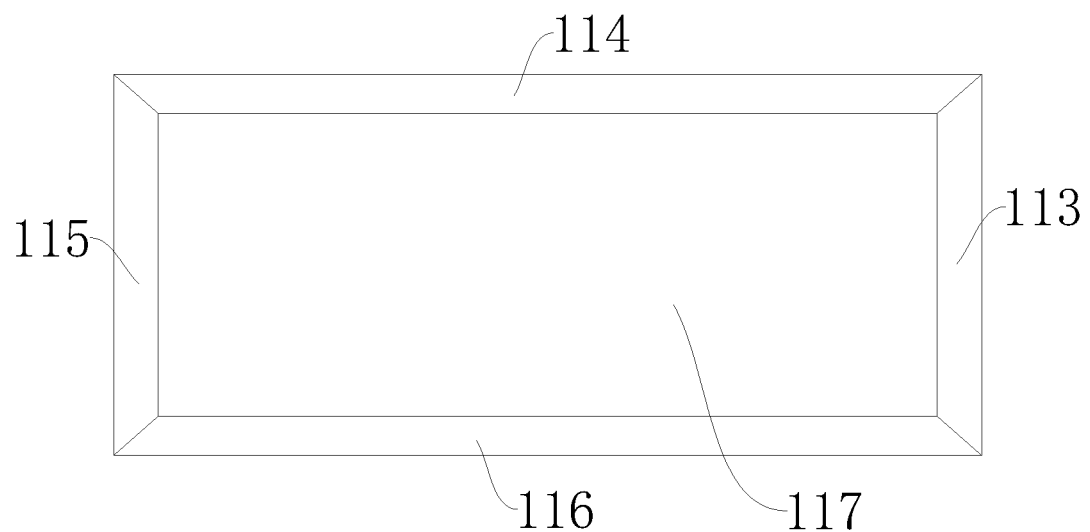
FIG. 7 is a schematic diagram of a housing in a multi-row ultrasonic imaging apparatus provided by an embodiment of the application.

Referring to FIG. 7, the housing 110 has a rectangular shape. The housing 110 includes a first sidewall 113, a second sidewall 114, a third sidewall 115, a fourth sidewall 116, and a bottom wall 117. The first sidewall 113, the second sidewall 114, the third sidewall 115, and the fourth sidewall 116 are connected end to end, and they are all connected to the bottom wall 117. The first ultrasonic transducer 120 is fixedly connected to the bottom wall 117. The drive member 151 is fixedly installed outside the first sidewall 113, and the movable member 152 extends into the first sidewall 113.

In the multi-row ultrasonic imaging apparatus 100 provided by this embodiment of the present application, the ultrasonic waves emitted by the first ultrasonic transducer 120 and the second ultrasonic transducer 130 can intersect to form a confocal point. At least one of the first ultrasonic transducer 120 and the second ultrasonic transducer 130 is connected to the adjustment mechanism to translate and/or rotate relative to the housing 100 under the action of the adjustment mechanism, thereby adjusting the position of the confocal point. Compared with the related art, the multi-row ultrasonic imaging apparatus 100 provided by the present application adopts an adjustment mechanism connected with the first ultrasonic transducer 120 and/or the second ultrasonic transducer 130, so it can accurately change the position of the confocal point. In addition, the multiple rows of transducers will not affect each other, which is practical and efficient, making the ultrasonic imaging instrument 10 cost-effective, provide a good user experience, and convenient for the user to quickly observe the depth of the confocal point, which is convenient and practical.

The foregoing merely depicts some illustrative embodiments of the application, and is not to be used to limit the application. For those skilled in the art, the application is subject to various modifications and changes. Any modification, equivalent replacement, improvement, etc. made within the spirit and principle of this application shall all be included in the scope of protection of this application.

What is claimed is:

1. A multi-row ultrasonic imaging apparatus, comprising: a housing; a first ultrasonic transducer; a second ultrasonic transducer; a third ultrasonic transducer; two limiting shafts; a first displacement mechanism; a second displacement mechanism; a first rotary mechanism; and a second rotary mechanism, wherein the first ultrasonic transducer, the second ultrasonic transducer, the third ultrasonic transducer, the first displacement mechanism, the second displacement mechanism, the first rotary mechanism and the second rotary mechanism are installed in the housing, wherein the first ultrasonic transducer is fixedly installed at the middle of the housing, wherein the second ultrasonic transducer and the third ultrasonic transducer are respectively arranged on two sides of the first ultrasonic transducer, wherein the first displacement mechanism and the first rotary mechanism are connected to the second ultrasonic transducer through one limiting shaft and the second displacement mechanism and the second rotary mechanism are connected to the third ultrasonic transducer through another limiting shaft, wherein the movements of the first displacement mechanism and the second displacement mechanism are configured to be kept in reverse synchronization, and the movements of the first rotary mechanism and the second rotary mechanism are configured to be kept in reverse synchronization, wherein a distance between the first ultrasonic transducer and the second ultrasonic transducer is configured to be always equal to a distance between the first ultrasonic transducer and the third ultrasonic transducer, and an angle formed by the first ultrasonic transducer and the second ultrasonic transducer is configured to be always kept the same as an angle formed by the first ultrasonic transducer and the third ultrasonic transducer, wherein the ultrasonic waves emitted by the first ultrasonic transducer, the second ultrasonic transducer, and the third ultrasonic transducer are configured to always converge at a common focal point.

2. The multi-row ultrasonic imaging apparatus of claim 1, wherein the first displacement mechanism comprises a drive member and a movable member, wherein the drive member is fixedly installed on the housing and connected to the movable member to drive the movable member to translate, wherein the movable member is extended into the housing and is fixedly connected to the limiting shaft, wherein the movable member is configured to be driven by the drive member to move away from the first ultrasonic transducer, wherein the second ultrasonic transducer is sleeved outside the one limiting shaft and is configured to rotate relative to the limiting shaft, wherein the movable member is configured to drive the second ultrasonic transducer to move away from the first ultrasonic transducer through the limiting shaft.

3. The multi-row ultrasonic imaging apparatus of claim 2, wherein the drive member is a motor, the movable member comprises a screw rod and a nut, wherein the drive member is connected to the screw rod to drive the screw rod to rotate, wherein the screw rod is extended into the housing, rotatably connected with the housing, and fitted with the nut, wherein the nut is configured to translate along an axial direction of the screw rod during the rotation of the screw rod, wherein the one limiting shaft is fixedly connected to an outer side of the nut and the nut is configured to drive the limiting shaft to move.

4. The multi-row ultrasonic imaging apparatus of claim 3, wherein a limiting stand is fixedly connected to a side surface of the first ultrasonic transducer, wherein the limiting stand defines a groove, and the screw rod is extended into the groove and configured to rotate relative to the groove.

5. The multi-row ultrasonic imaging apparatus of claim 1, wherein the first rotary mechanism comprises a rotary motor and a transmission member, wherein the rotary motor is fixedly mounted on the second ultrasonic transducer and is connected to the one limiting shaft through the transmission member, wherein the rotary motor is provided to drive the second ultrasonic transducer to rotate relative to the one limiting shaft through the transmission member, wherein the angle between the first ultrasonic transducer and the second ultrasonic transducer is to be changed.

6. The multi-row ultrasonic imaging apparatus of claim 5, wherein the transmission member comprises a first gear and a second gear, wherein the first gear is sleeved outside an output shaft of the rotary motor and is fixedly connected to the output shaft, wherein the second gear is sleeved outside the one limiting shaft and fixedly connected to the one limiting shaft, wherein the first gear is engaged with the second gear.

7. The multi-row ultrasonic imaging apparatus of claim 6, wherein the housing defines a limiting slot, wherein the limiting slot has an extension direction the same as that of the movable member, wherein the one limiting shaft passes through the second ultrasonic transducer and is extended into the limiting slot, wherein the one limiting shaft is slidably fitted with the limiting slot, wherein the limiting slot is configured to limit the one limiting shaft to prevent the nut from rotating along with the screw rod.

\* \* \* \* \*